US00PP32421P2

(12) United States Plant Patent
Saunders

(10) Patent No.: US PP32,421 P2
(45) Date of Patent: Nov. 3, 2020

(54) ***BUXUS* PLANT NAMED 'SB 300'**

(50) Latin Name: ***Buxus microphylla* var. *japonica***
Varietal Denomination: SB 300

(71) Applicant: Saunders Genetics, LLC, Piney River, VA (US)

(72) Inventor: Julian Bennett Saunders, Roseland, VA (US)

(73) Assignee: SAUNDERS GENETICS, LLC, Piney River, VA (US)

( * ) Notice: Subject to any disclaimer, the term of this patent is extended or adjusted under 35 U.S.C. 154(b) by 0 days.

(21) Appl. No.: 16/602,862

(22) Filed: Dec. 12, 2019

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Buxus*, 'SB 300', that is characterized by its tight, upright and very compact plant habit, its foliage that are dark green in color, and its new growth that is new growth that is fresh and vigorous.

2 Drawing Sheets

Botanical classification: *Buxus microphylla* var. *japonica*.
Variety denomination: 'SB 300'.

BACKGROUND OF THE INVENTION

The present invention relates to a new and distinct cultivar of *Buxus microphylla* var. *japonica* and will be referred to hereafter by its cultivar name, 'SB 300'. 'SB 300' is a new cultivar of boxwood grown for use as an ornamental landscape plant.

The Inventor discovered the new cultivar in summer of 2007 as a new and unique plant in a container block of *Buxus microphylla* 'Wintergreen' (not patented) in his nursery in Piney River, Va. As the containers had been planted with stem cuttings of 'Wintergreen', it is presumed that the new cultivar arose as a branch mutation of 'Wintergreen'.

Asexual propagation of the new cultivar was first accomplished by the Inventor by stem cuttings in summer of 2008 in Piney River, Va. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'SB 300' as a unique cultivar of *Buxus*.

1. 'SB 300' exhibits a tight, upright and very compact plant habit.
2. 'SB 300' exhibits foliage that are dark green in color.
3. 'SB 300' exhibits new growth that is fresh and vigorous.

The parent plant of 'SB 300', 'Wintergreen', differs from 'SB 300' in having new growth that is less fresh and vigorous, a more open, spreading and loose growth habit, and leaves that are paler green in color. 'SB 300' can be most closely compared to *Buxus microphylla* cultivars 'Wintergem' (not patented) and 'Jim Stauffer' (not patented). 'Wintergem' is similar to 'SB 300' in leaf size and shape and cold hardiness. 'Wintergem' differs from 'SB 300' in having a less compact, less upright plant habit, foliage that is less dense, and foliage that is lighter green in color. 'Jim Stauffer' is similar to 'SB 300' in overall growth rate and cold hardiness. 'Jim Stauffer' differs from 'SB 300' in having a less tight growth habit, a less upright plant habit and foliage that is lighter green in color.

BRIEF DESCRIPTION OF THE DRAWINGS

The accompanying colored photographs illustrate the overall appearance and distinct characteristics of the new *Buxus*. The photographs were taken of two-year-old plants as grown in a cold frame (covered in plastic in winter) at a nursery in Piney River, Va. The photographs in FIG. 1 and FIG. 2 were taken of a plant 5 years in age.

The photograph in FIG. 1 provides a side view of 'SB 300'.

Figure 1:
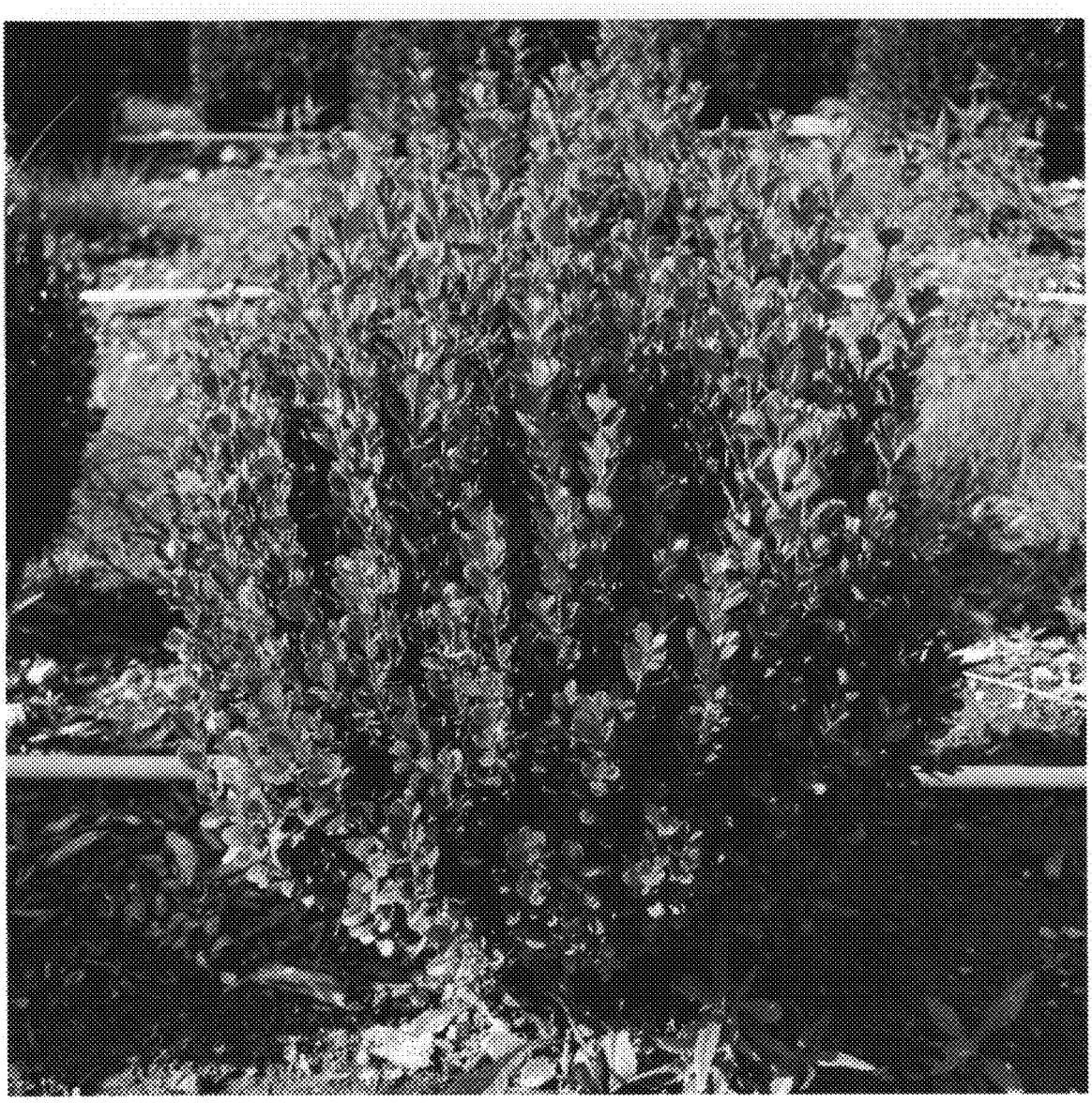
Figure 2:
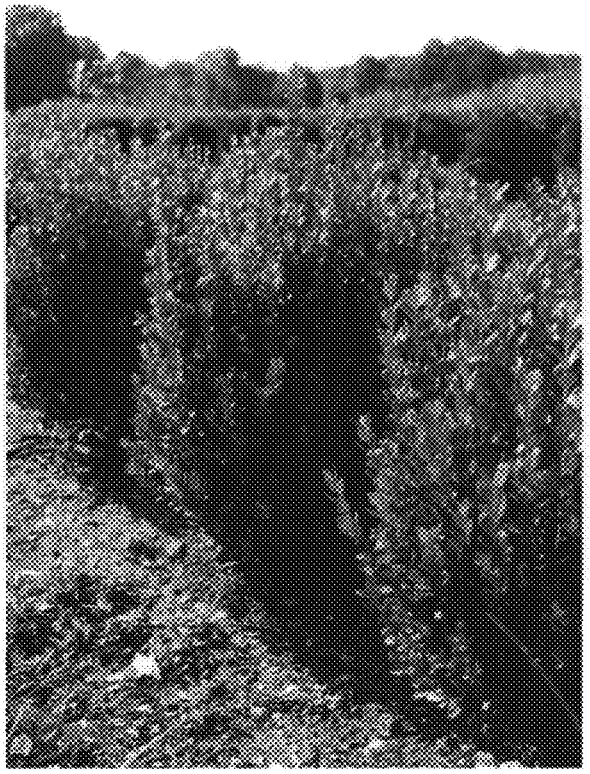

The photograph in FIG. 2 provides a side view of the compact plant habit of 'SB 300' taken of a plant 6 years in age.

Figure 3:
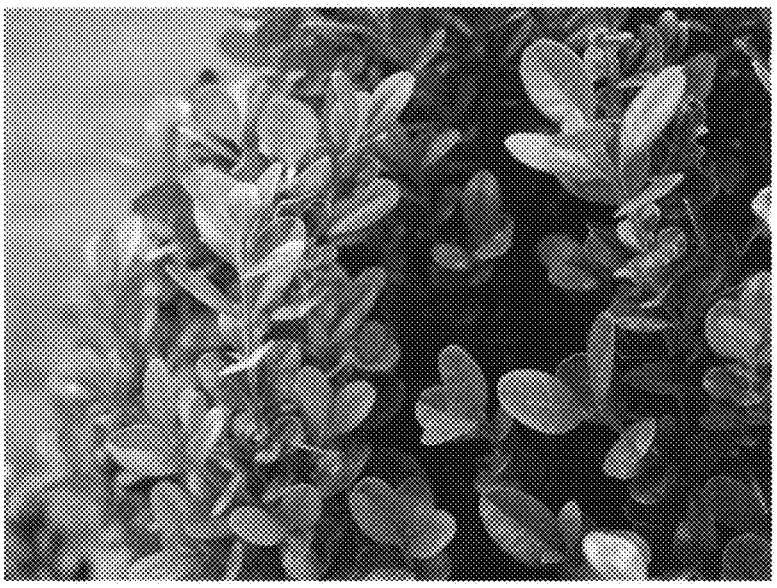

The photograph in FIG. 3 provides a close-up view of the new foliage growth of 'SB 300'.

The colors in the photographs are as close as possible with the photographic and printing technology utilized and the color values cited in the detailed botanical description accurately describe the colors of the new *Buxus*.

DETAILED BOTANICAL DESCRIPTION

The following is a description of two-year-old plants of the new cultivar as grown in a cold frame (covered in plastic in winter) in one-gallon containers at a nursery in Piney River, Va. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Compact, upright.

*Height and spread*.—Reaches an average of 17 cm in width and 25 cm in height as grown in a one-gallon container, 5-year-old plant in the landscape reaches an average of 45 cm in length and spread.

*Hardiness*.—At least in U.S.D.A. Zones 5 to 8.

*Diseases resistance*.—Very good tolerance to boxwood blight (*Cylindrocladium buxicola*) and good resistance to *Phytophthora* sp.

*Root description*.—Fibrous, 161C in color.

*Propagation*.—Stem cuttings.

*Root development*.—Cuttings take 6 weeks to initiate rooting, 1 year to fill a 4-quart container.

*Growth rate*.—Vigorous, 10 to 15 cm per year.

Branch description:

*Branch shape*.—Quadrangular.

*Branch color*.—Young stems; 144A and 149A, mature stem and bark; a blend of 158A and 197A.

*Branch size*.—Main branches; average of 6 cm in length and 3 cm in diameter, lateral branches emerging from main stems; average of 17 cm in length and 2 mm in diameter, tertiary branches emerging from the lateral branches; average of 9 cm in length and 2 mm in diameter.

*Stem strength*.—Strong.

*Stem surface*.—Young stems; glabrous and smooth, mature and older stems; a blend of glabrous and rugose bark, dull.

*Branch number*.—An average of 4 main branches, average number of branches per main stem; an average of 7 lateral branches emerging from main stems and an average of 4 tertiary branches emerging from the lateral branches.

*Branching habit*.—Stems arise from base, branches held in multiple tight angles and upright.

Foliage description:

*Leaf shape*.—Orbicular to ovate.

*Leaf division*.—Simple.

*Leaf base*.—Rounded.

*Leaf apex*.—Retuse.

*Leaf fragrance*.—Slightly pungent.

*Leaf venation*.—Pinnate, color matches leaf surface.

*Leaf margins*.—Entire.

*Leaf arrangement*.—Opposite.

*Leaf attachment*.—Petiolate.

*Internode length*.—Average of 1 cm.

*Leaf surface*.—Glabrous and shiny on both surfaces.

*Leaf texture*.—Slightly thick, tough and waxy.

*Leaf size*.—Up to an average of 2 cm in length and 1.7 cm in width.

*Leaf quantity*.—Average of 30 on a branch 15 cm in length.

*Leaf color*.—Young leaves; upper and lower surface 144A, mature leaves; upper surface NN137A, lower surface 144A.

*Petioles*.—Average of 1 mm in length and 0.5 mm in width, both sides are 144B in color and glabrous.

Inflorescence description: No flowers have been observed, in general plants of *Buxus microphylla* typically don't flower unless under stress or over 10 years in age.

It is claimed:

1. A new and distinct cultivar of *Buxus* plant named 'SB 300' as herein illustrated and described.

* * * * *